US011596297B2

(12) United States Patent
Yoshinaga et al.

(10) Patent No.: US 11,596,297 B2
(45) Date of Patent: Mar. 7, 2023

(54) INSERTION APPARATUS AND OPERATION SECTION OF INSERTION APPARATUS

(71) Applicant: OLYMPUS CORPORATION, Tokyo (JP)

(72) Inventors: Takuto Yoshinaga, Hino (JP); Tsukasa Ota, Hachioji (JP); Xiongwei Wang, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 290 days.

(21) Appl. No.: 16/907,420

(22) Filed: Jun. 22, 2020

(65) Prior Publication Data

US 2020/0315426 A1 Oct. 8, 2020

Related U.S. Application Data

(63) Continuation of application No. PCT/JP2018/039108, filed on Oct. 19, 2018.

(30) Foreign Application Priority Data

Dec. 22, 2017 (JP) .............................. JP2017-247014

(51) Int. Cl.
*A61B 1/005* (2006.01)
*A61B 1/00* (2006.01)
(Continued)

(52) U.S. Cl.
CPC ........ *A61B 1/0055* (2013.01); *A61B 1/00066* (2013.01); *A61B 1/00094* (2013.01);
(Continued)

(58) Field of Classification Search
CPC ............ A61B 1/00066; A61B 1/00119; A61B 1/00137; A61B 1/0125; A61B 1/015
See application file for complete search history.

(56) References Cited

U.S. PATENT DOCUMENTS 5,037,386 A * 8/1991 Marcus .................... A61B 5/03
600/156
6,282,442 B1 * 8/2001 DeStefano ............ A61M 1/774
606/49

(Continued)

FOREIGN PATENT DOCUMENTS

CN 105310632 A 2/2016
EP 1 527 797 A1 5/2005
(Continued)

OTHER PUBLICATIONS

International Search Report dated Dec. 4, 2018 issued in International Application No. PCT/JP2018/039108.

*Primary Examiner* — Matthew J Kasztejna

(74) *Attorney, Agent, or Firm* — Scully, Scott, Murphy & Presser, P.C.

(57) ABSTRACT

An insertion apparatus includes: a tube in which a water feeding communication hole opens on an outer peripheral surface of the tube; a tube connector in which a water feeding branch conduit which allows an inner surface of a tube insertion hole to communicate with an outside is formed, and a second stopper portion which protrudes toward the inside of the tube insertion hole is formed; an O ring which is positioned by contacting with the second stopper portion; a spacer which is positioned by contacting with the O ring, and in which a communication hole which allows an inner surface side and an outer surface side of a wall portion to communicate with each other is formed; and an O ring which is positioned by contacting with the spacer.

21 Claims, 13 Drawing Sheets

(51) Int. Cl.
*A61B 1/01* (2006.01)
*A61B 1/012* (2006.01)
*A61B 1/015* (2006.01)
A61B 1/05 (2006.01)
A61B 1/06 (2006.01)
A61B 1/273 (2006.01)

(52) U.S. Cl.
CPC ...... *A61B 1/00119* (2013.01); *A61B 1/00135* (2013.01); *A61B 1/00137* (2013.01); *A61B 1/01* (2013.01); *A61B 1/015* (2013.01); *A61B 1/0125* (2013.01); *A61B 1/05* (2013.01); *A61B 1/0676* (2013.01); *A61B 1/2736* (2013.01)

(56) References Cited

U.S. PATENT DOCUMENTS

| | | | |
|---|---|---|---|
| 7,892,167 B2 * | 2/2011 | Francisco | A61B 1/015 600/117 |
| 8,893,722 B2 * | 11/2014 | Emanuel | A61B 90/30 606/15 |
| 8,951,274 B2 * | 2/2015 | Adams | A61B 17/32002 606/171 |
| 2005/0095891 A1 | 5/2005 | Schorn | |
| 2011/0282150 A1 | 11/2011 | Yamakawa et al. | |
| 2012/0004507 A1 | 1/2012 | Kaye | |
| 2016/0029878 A1 | 2/2016 | Yamazaki et al. | |

FOREIGN PATENT DOCUMENTS

| | | |
|---|---|---|
| EP | 2 386 241 A2 | 11/2011 |
| JP | 2003-169774 A | 6/2003 |
| JP | 2005-131413 A | 5/2005 |
| JP | 2009-039205 A | 2/2009 |
| JP | 2011-167460 A | 9/2011 |
| JP | 2011-235005 A | 11/2011 |
| JP | 2014-092564 A | 5/2014 |
| WO | 2007/120713 A2 | 10/2007 |

* cited by examiner

INSERTION APPARATUS AND OPERATION SECTION OF INSERTION APPARATUS

CROSS REFERENCE TO RELATED APPLICATION

This application is a continuation application of PCT/JP2018/039108 filed on Oct. 19, 2018 and claims benefit of Japanese Application No. 2017-247014 filed in Japan on Dec. 22, 2017, the entire contents of which are incorporated herein by this reference.

BACKGROUND OF THE INVENTION

1. Field of the Invention

The present invention relates to an insertion apparatus where an insertion section which can be inserted into a subject is formed using a tube, and an operation section of the insertion apparatus.

2. Description of the Related Art

Conventionally, in a medical field, endoscopes have been widely used where an internal organ or the like in a body cavity can be observed by inserting an elongated insertion section into the body cavity.

There may be a case where such an endoscope is used in combination with a separate insertion apparatus and the like depending on various procedures, inspections or the like. For example, as an endoscope apparatus where an endoscope and an insertion apparatus are used in combination, a so-called mother-baby endoscope which is used in the observation or the treatment of the inside of bile duct or the inside of pancreatic duct has been put into practice.

The mother-baby endoscope is configured such that a baby endoscope having a narrow diameter which forms an insertion apparatus is inserted into a treatment instrument channel or the like of an endoscope of a normal size which forms a mother endoscope (for example, an endoscope for duodenum). Such mother-baby endoscope is introduced into a body cavity so as to perform the observation or the treatment of the inside of a bile duct or the inside of the pancreatic duct.

As an insertion apparatus of this type, there has been known an insertion apparatus where an insertion section is formed by using a tube such as a multi-lumen tube having a narrow diameter. In this case, to allow the insertion apparatus to realize various treatments such as air feeding, water feeding or suction, it is necessary to configure the insertion apparatus such that a frame member such as a tube connector is connected to a proximal end side of the tube, and a predetermined hole formed in the tube is connected to a communication hole such as a conduit mounted in the frame member in a gas-tight or liquid-tight state.

In view of the above, for example, Japanese Patent Application Laid-Open Publication No. 2003-169774 discloses a technique where an air supply passage end portion opening, a water feeding passage end portion opening and a suction passage end portion opening having a circumferential groove shape are formed in an inner peripheral surface of a connection hole formed in a tube connector, O rings for sealing are mounted at positions where the O rings sandwich the above-mentioned openings in the respective axially distal end direction, and in a state where a gap formed between the inner peripheral surface of the connection hole and an outer peripheral surface of the tube are sealed by the respective O rings, an air supply side hole, a water feeding side hole and a suction side hole formed in the tube are made to communicate with an air supply communication passage, a water feeding communication passage and a suction communication passage through the air supply passage end portion opening, the water feeding passage end portion opening and the suction passage end portion opening.

SUMMARY OF THE INVENTION

According to an aspect of the present invention, there is provided an insertion apparatus including: a tube which includes at least one longitudinal direction hole extending from a distal end side to a proximal end side along the tube in a longitudinal direction, and in which a first communication hole allowing the longitudinal direction hole to communicate with an outside opens on an outer peripheral surface; a frame member including a tube insertion hole into which the tube is inserted and a second communication hole which allows the tube insertion hole to communicate with the outside; and a spacer mounted on the tube exteriorly, the spacer positioned in the tube insertion hole, the spacer allowing the first communication hole and the second communication hole to communicate with each other.

According to another aspect of the present invention, there is provided an operation section of an insertion apparatus, the operation section including: a tube which includes at least one longitudinal direction hole extending from a distal end side to a proximal end side along the tube in a longitudinal direction, and in which a first communication hole allowing the longitudinal direction hole to communicate with an outside opens on an outer peripheral surface; a frame member which has a tube insertion hole into which the tube is inserted and a second communication hole which allows the tube insertion hole to communicate with the outside; and a spacer which is mounted on the tube exteriorly, the spacer positioned in the tube insertion hole, the spacer allowing the first communication hole and the second communication hole to communicate with each other.

DETAILED DESCRIPTION OF THE PREFERRED EMBODIMENTS

Figure 2:
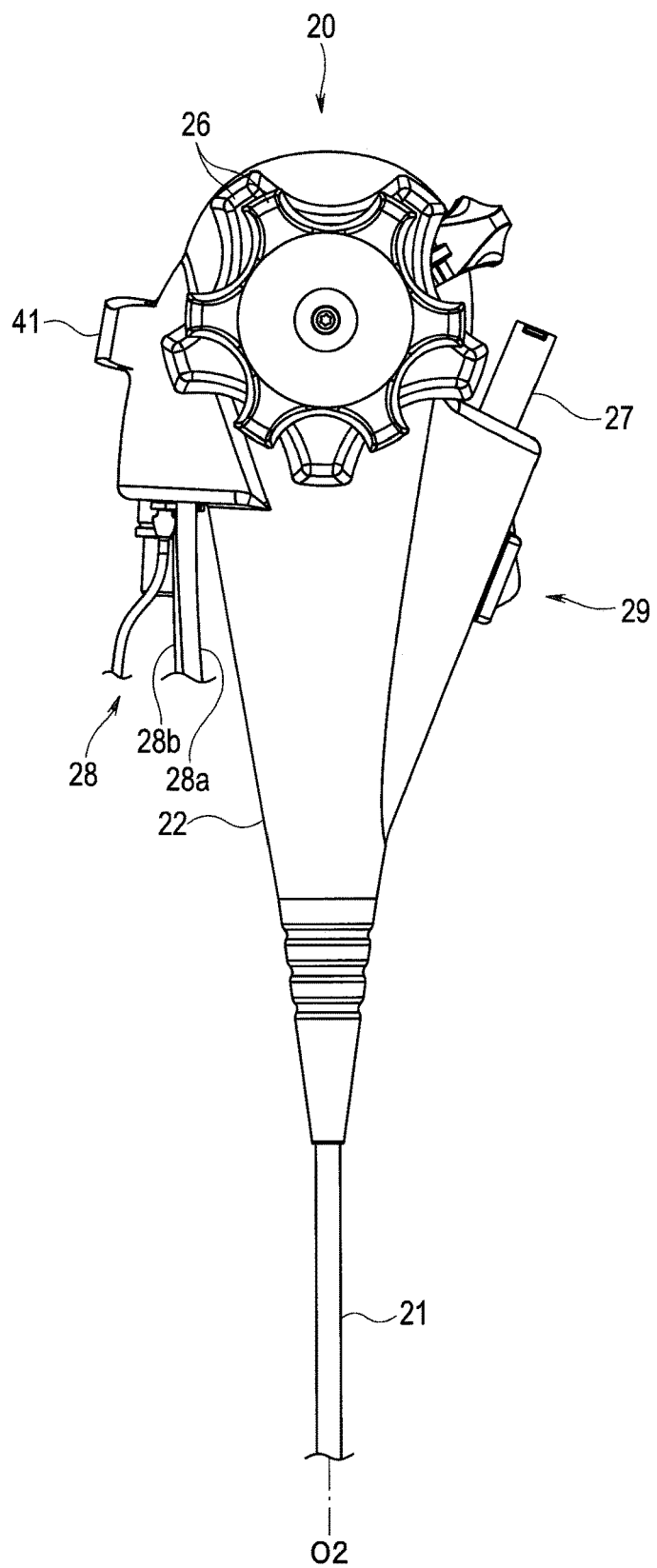
FIG. 2 is a plan view showing a configuration of a baby endoscope.
Figure 3:
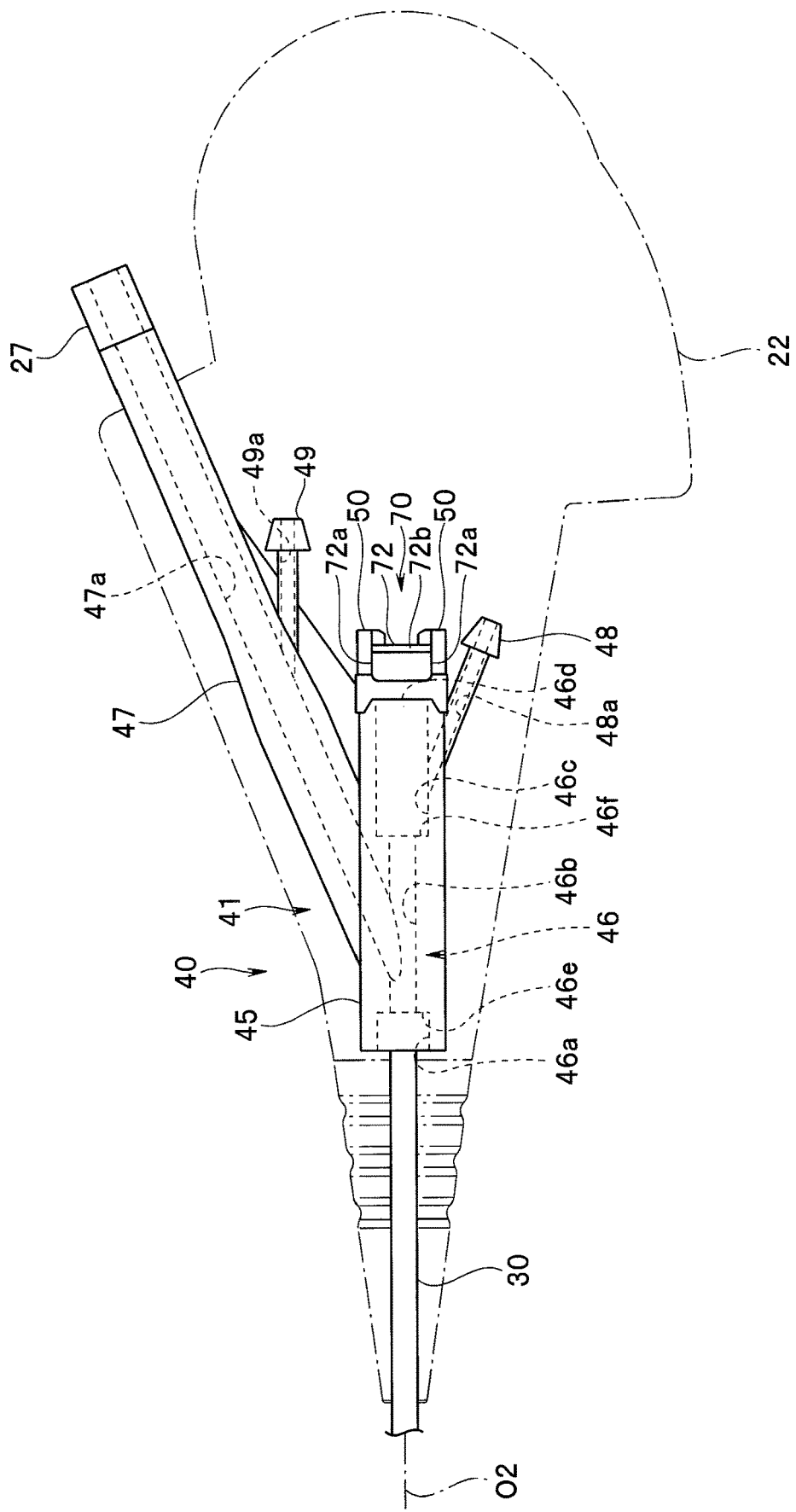
FIG. 3 is a plan view showing a tube module disposed in an operation section.
Figure 4:
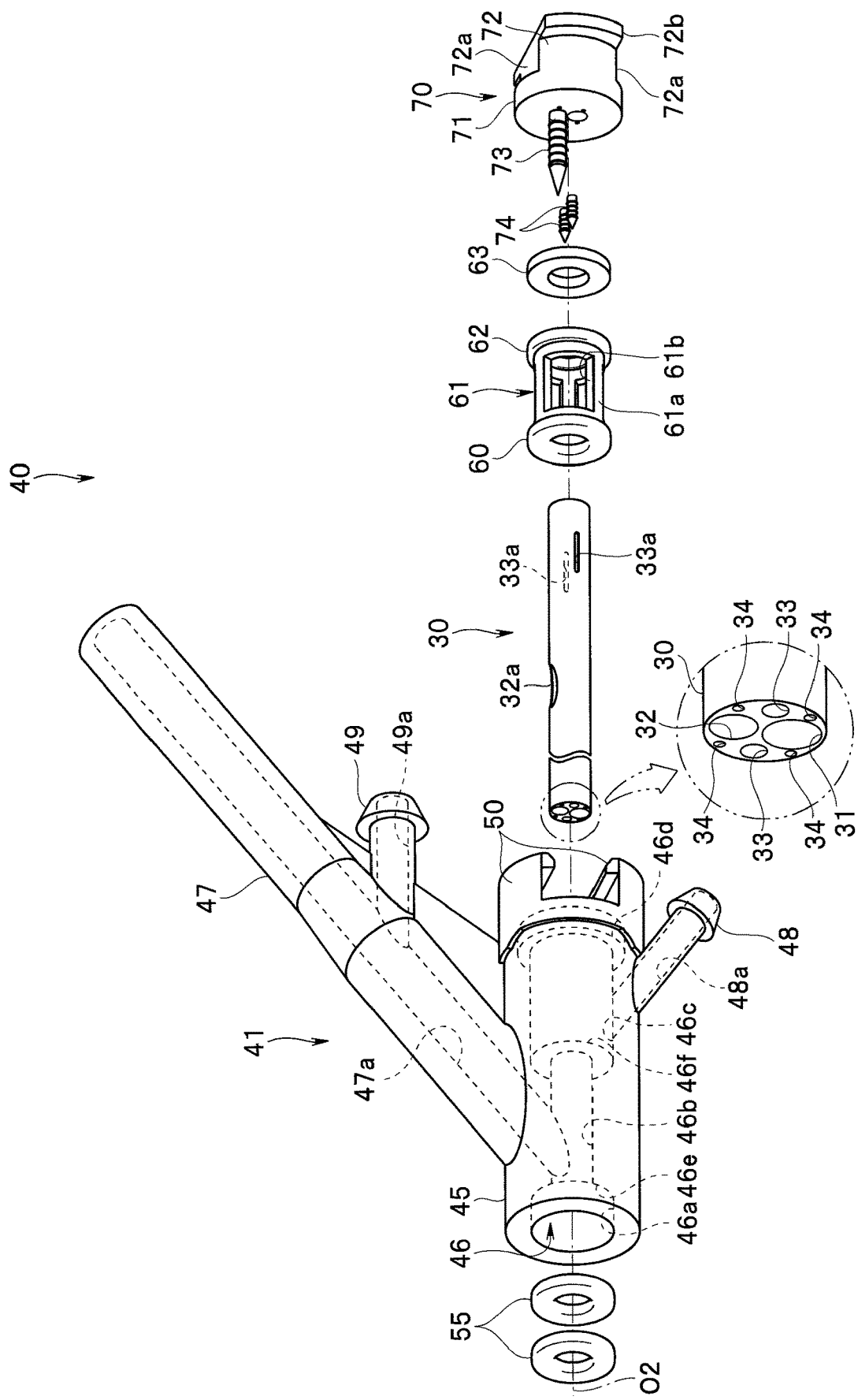
FIG. 4 is an exploded perspective view of the tube module.
Figure 5:
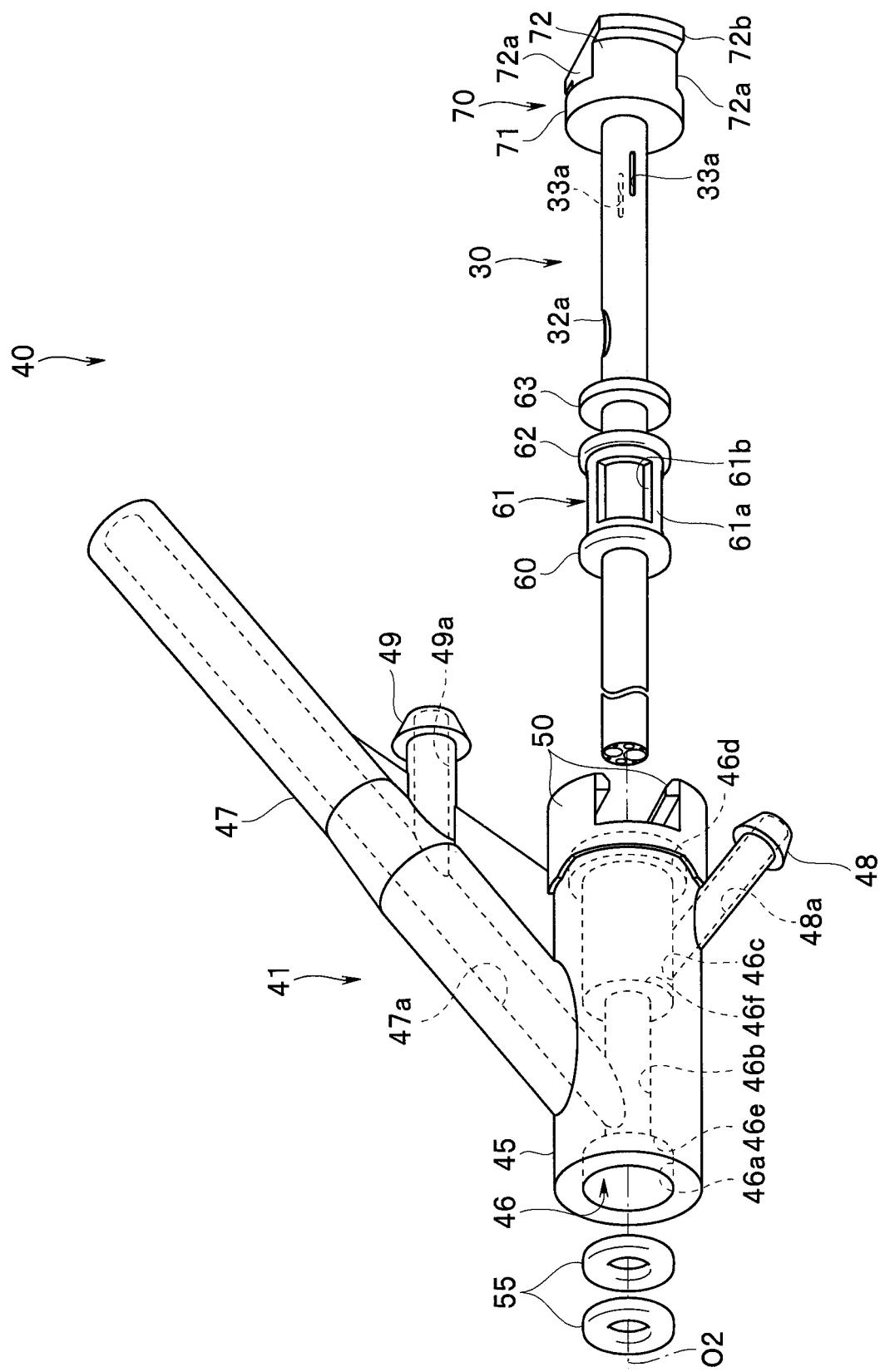
FIG. 5 is a perspective view showing a state at a time of assembling the tube module.
Figure 6:
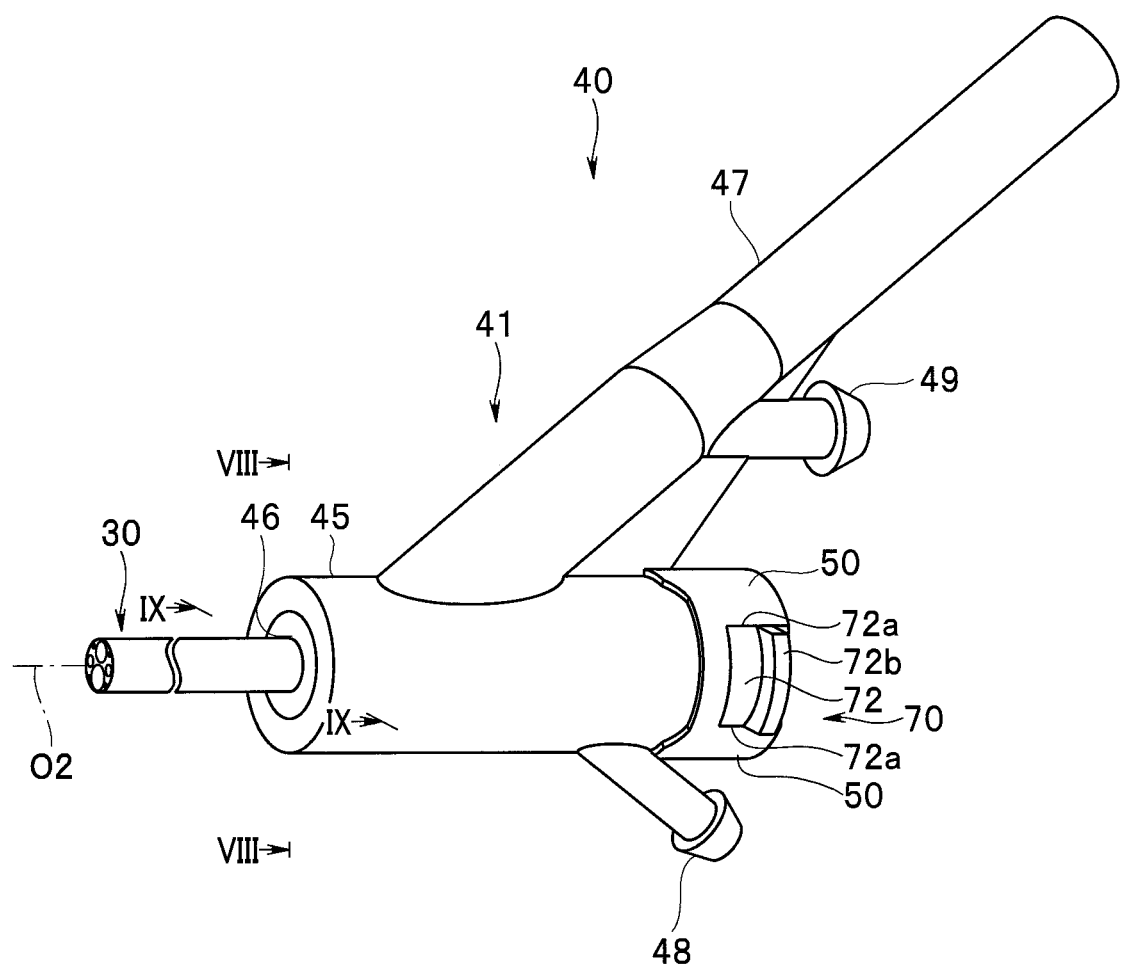
FIG. 6 is a perspective view of the tube module.
Figure 7:
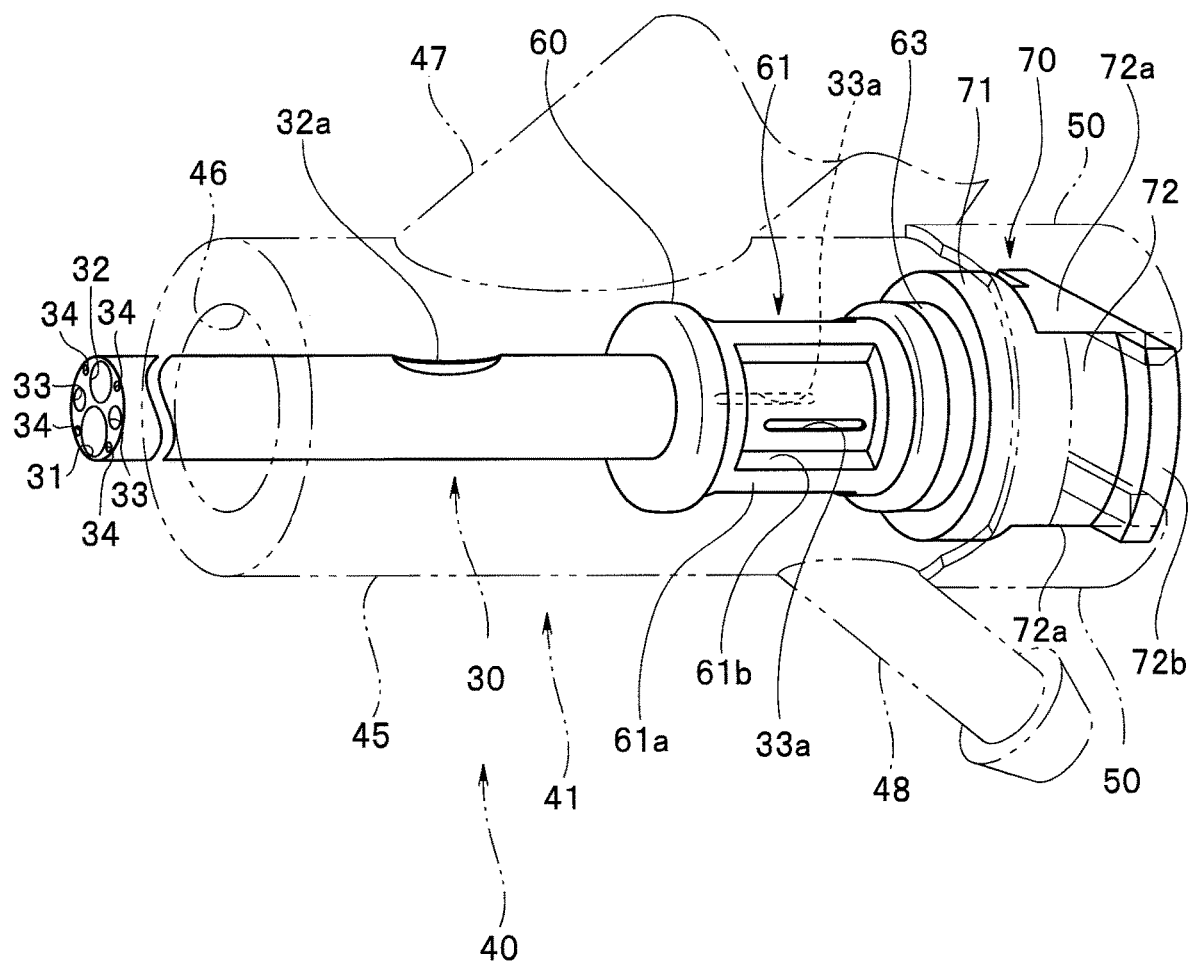
FIG. 7 is an explanatory diagram showing an arrangement of a sealing member and a spacer in the tube module.
Figure 8:
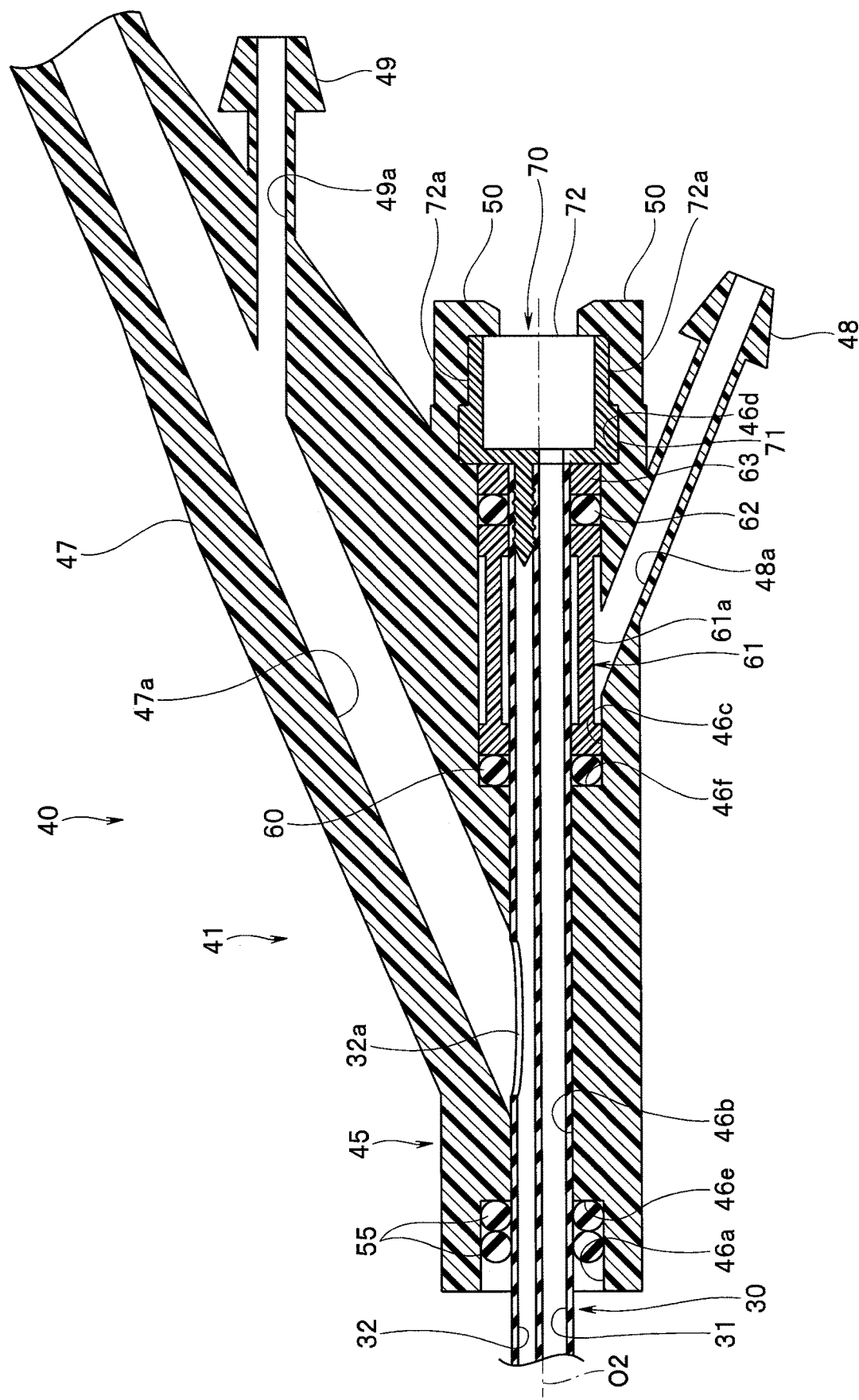
FIG. 8 is a perspective view of the tube module taken along a line VIII-VIII in FIG. 6.
Figure 9:
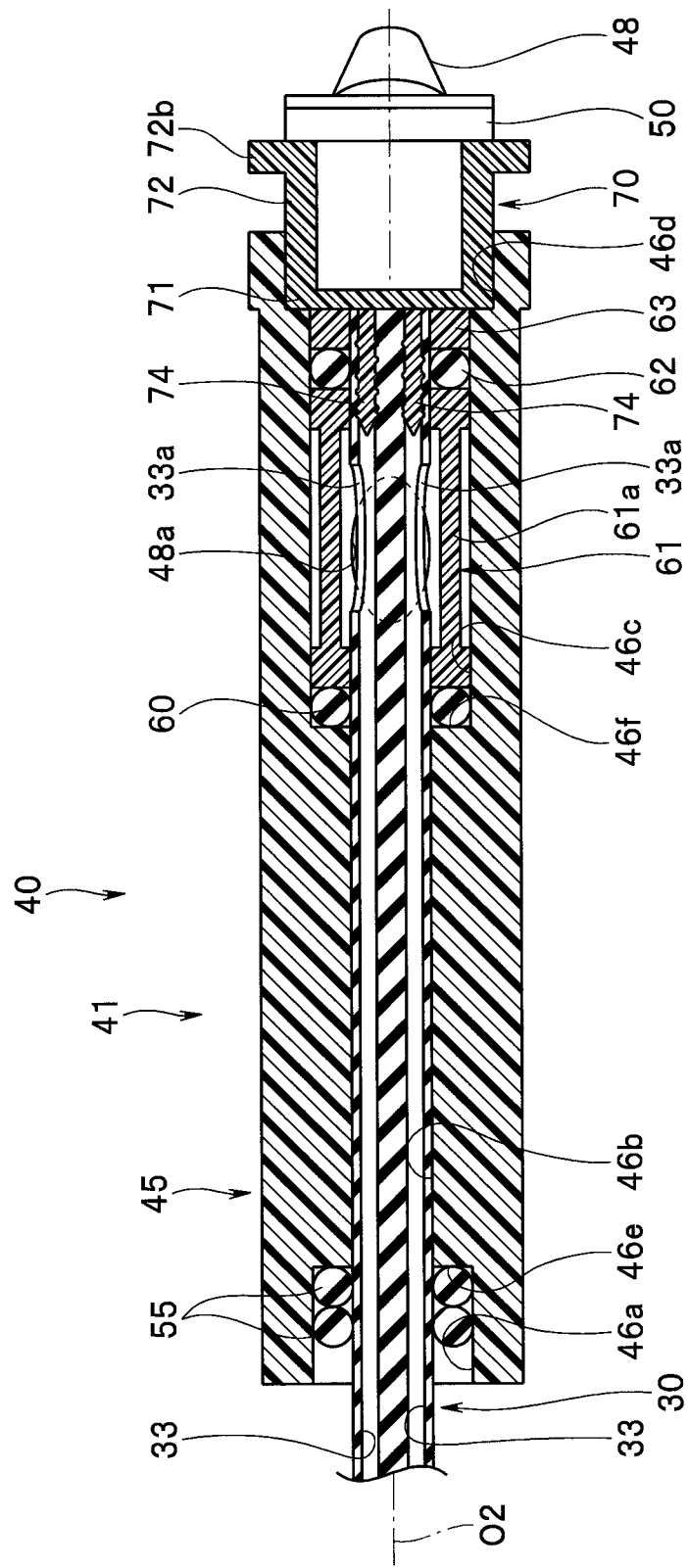
FIG. 9 is a perspective view of the tube module taken along a line IX-IX in FIG. 6.
Figure 10:
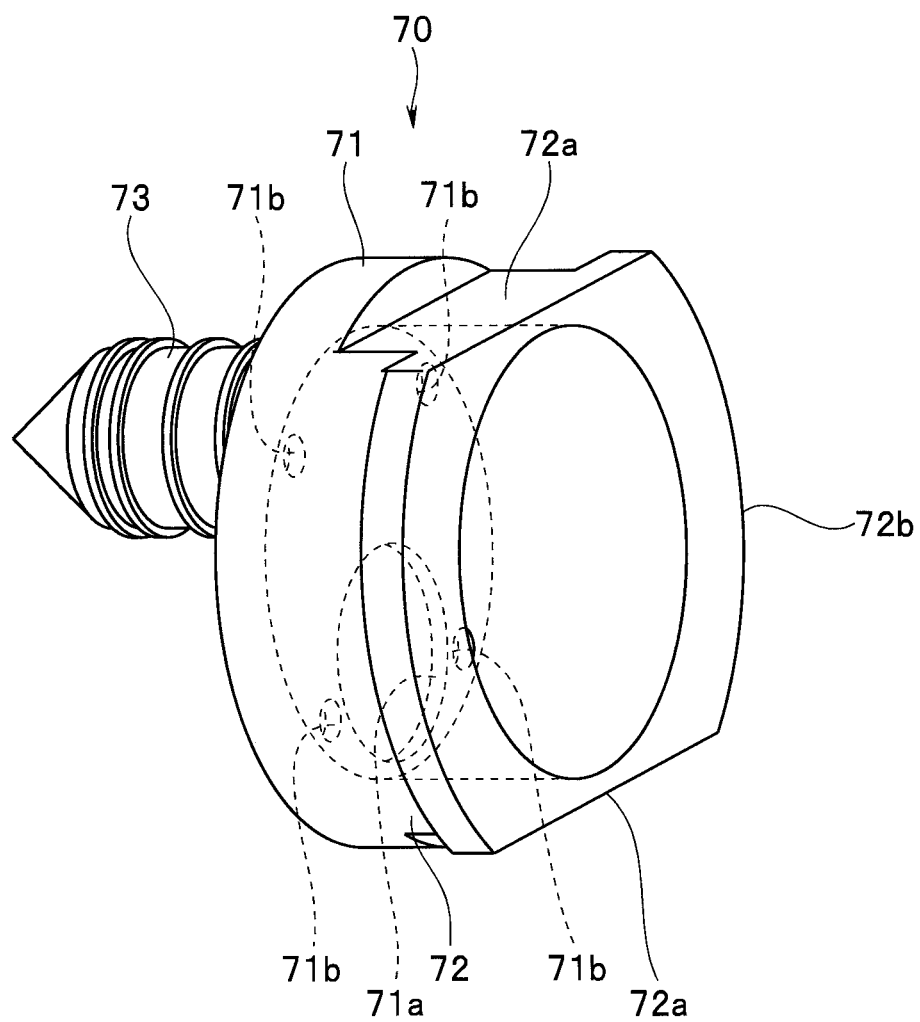
FIG. 10 is a perspective view of a stopper member.
Figure 11:
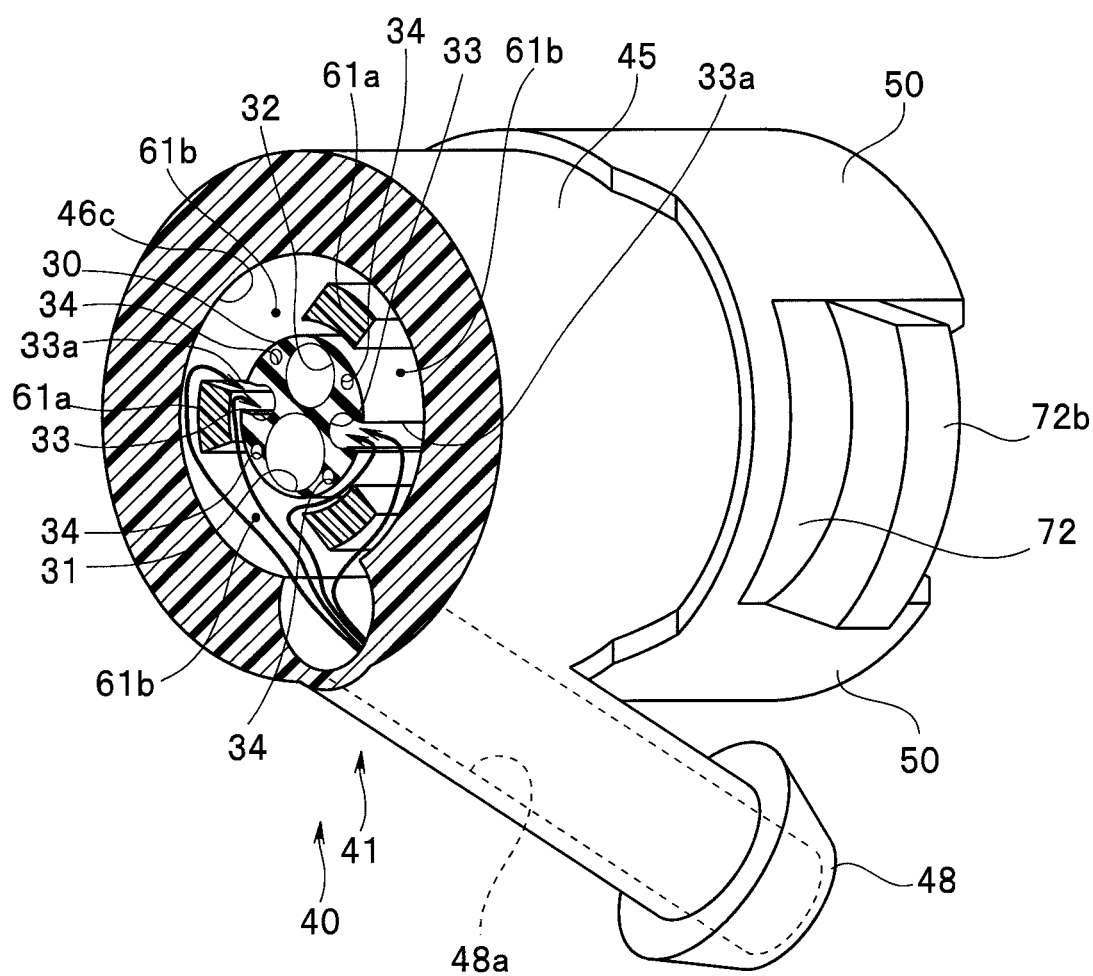
FIG. 11 is a perspective view of a cross section of the tube module.
Figure 12:
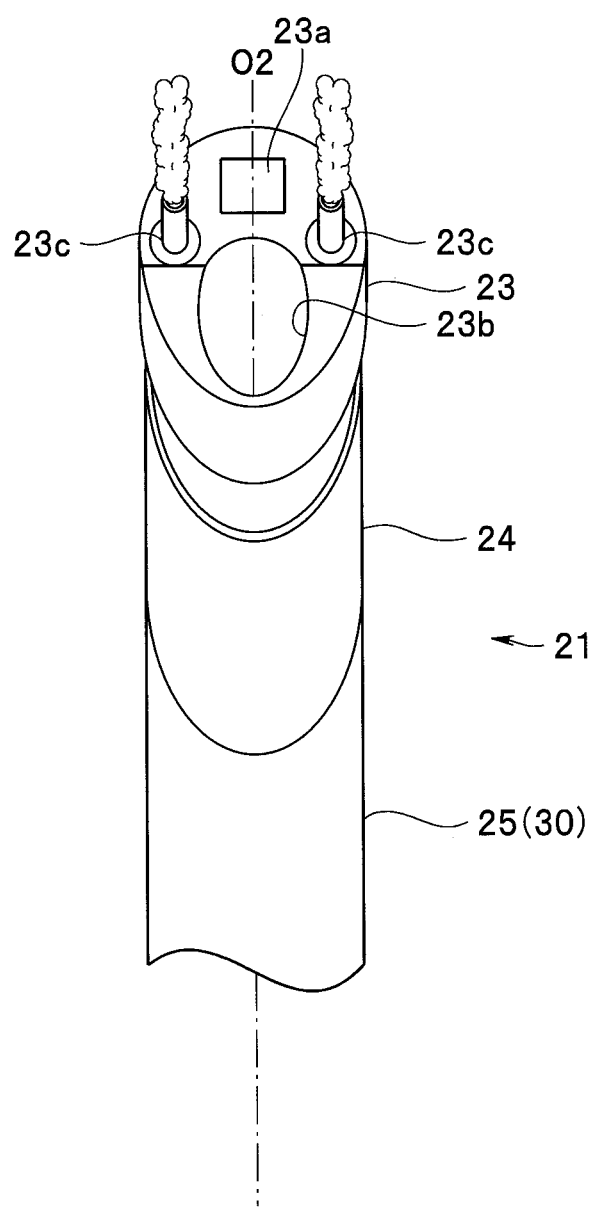
FIG. 12 is a perspective view showing a distal end portion of the baby endoscope.

Hereinafter, an embodiment of the present invention is described with reference to drawings. The drawings describe one embodiment of the present invention, wherein FIG. 1 is a plan view showing a configuration of an endoscope apparatus, FIG. 2 is a plan view showing a configuration of a baby endoscope, FIG. 3 is a plan view showing a tube module disposed in an operation section, FIG. 4 is an exploded perspective view of the tube module, FIG. 5 is a perspective view showing a state at a time of assembling the tube module, FIG. 6 is a perspective view of the tube module, FIG. 7 is an explanatory diagram showing an arrangement of a sealing member and a spacer in the tube module, FIG. 8 is a perspective view of the tube module taken along a line VIII-VIII in FIG. 6, FIG. 9 is a perspective view of the tube module taken along a line IX-IX in FIG. 6, FIG. 10 is a perspective view of a stopper member, FIG. 11 is a perspective view of a cross section of the tube module, and FIG. 12 is a perspective view showing a distal end portion of the baby endoscope.

Figure 1:
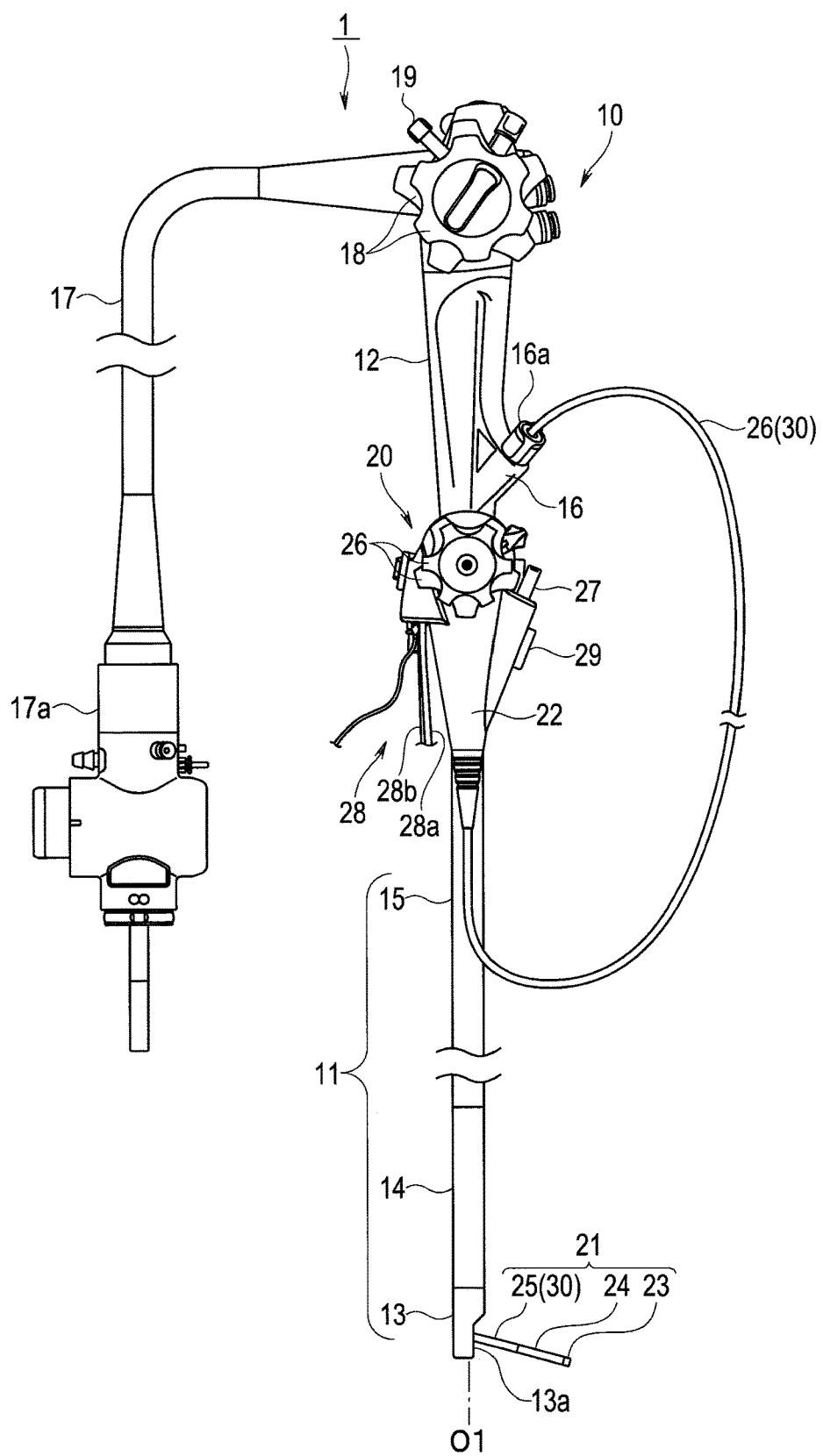
FIG. 1 is a plan view showing a configuration of an endoscope apparatus.

An endoscope apparatus 1 shown in FIG. 1 is a so-called mother-baby endoscope apparatus which includes a mother endoscope 10 forming an endoscope and a baby endoscope 20 forming an insertion apparatus fixed to the mother endoscope 10. In the embodiment, the baby endoscope 20 is, for example, a disposable insertion apparatus which is discarded after being used.

The mother endoscope 10 is formed of an insertion section 11 having an elongated shape which is inserted into a subject, and an operation section 12 which is connected to a proximal end side of the insertion section 11.

The insertion section 11 is formed by connecting a distal end portion 13, a bending portion 14, and a flexible tube portion 15 to one another in order from a distal end side.

In the distal end portion 13, for example, an image pickup unit which includes an object optical system and an image sensor such as a CCD or CMOS, and an illumination optical system which emits an illumination light transmitted through a light guide bundle (neither not shown) are disposed. In the embodiment, an optical axis of the image pickup unit and the illumination optical system is inclined with respect to a longitudinal axis (insertion axis O1) of the insertion section 11 by a predetermined angle. With such a configuration, the mother endoscope 10 forms a side view/oblique view type endoscope.

An opening portion 13*a* which opens sideward is formed on the distal end portion 13, and a distal end side of a treatment instrument channel (not shown) which is made to pass through the insertion section 11 is made to communicate with the opening portion 13*a*. In such a configuration, it is possible to allow, for example, an insertion section 21 of the baby endoscope 20 to pass through the treatment instrument channel besides a treatment instrument or the like.

Further, a treatment instrument raising base (not shown) is formed on the opening portion 13*a*. The treatment instrument raising base is provided for raising the treatment instrument which protrudes from the opening portion 13*a* through the treatment instrument channel, the insertion section 21 of the baby endoscope 20 or the like.

A bending block set formed by, for example, connecting a plurality of bending blocks (not shown) along an insertion axis O1 direction is disposed in the bending portion 14. With such a configuration, the bending portion 14 can actively bend in all directions about the insertion axis O1 including upward, downward, leftward, and rightward directions (UP-DOWN/RIGHT-LEFT).

The flexible tube portion 15 is formed of a tubular member which is passively bendable and has flexibility.

A treatment instrument insertion portion 16 is formed on a distal end side of the operation section 12, and a proximal end side of the treatment instrument channel is made to communicate with the treatment instrument insertion portion 16. A disposable forceps plug 16*a* is detachably mounted on the treatment instrument insertion portion 16.

On a proximal end side of the operation section 12, a pair of bending operation knobs 18 for performing a bending operation of the bending portion 14, an operation lever 19 for operating the treatment instrument raising base and the like are mounted.

A universal cable 17 extends from a side portion of the operation section 12 on the proximal end side, and an endoscope connector 17*a* which is detachably mounted on an external equipment such as a light source device (not shown) is mounted on an extending end of the universal cable 17.

The baby endoscope 20 is formed of the insertion section 21 having an elongated shape, and an operation section 22 which is connected to a proximal end side of the insertion section 21.

The insertion section 21 is formed by connecting a distal end portion 23, a bending portion 24, and a flexible tube portion 25 in order from a distal end side.

In the distal end portion 23, for example, an observation optical system which is connected to an image guide bundle, and an illumination optical system which emits an illumination light transmitted through a light guide bundle (neither shown) are disposed. These systems are disposed inside an observation window 23*a* (see FIG. 12) formed on a distal end surface of the distal end portion 23. In the embodiment, an optical axis of the image pickup unit and the illumination optical system is set along a longitudinal axis (insertion axis O2) of the insertion section 21. With such a configuration, the baby endoscope 20 forms a front-view type endoscope.

An opening portion 23*b* which opens frontward is formed on the distal end portion 23, and a pair of water feeding nozzles 23*c* is mounted on the distal end portion 23.

The bending portion 24 is formed, for example, by arranging a bending tube made of metal having elasticity (not shown) in the bending portion 24. The bending portion 24 is actively bendable in all directions about the insertion axis O2 including upward, downward, leftward, and rightward directions (UP-DOWN/RIGHT-LEFT).

The flexible tube portion 25 is formed of a tube 30 which is passively bendable and has flexibility. The tube 30 has at least one hole extending from a distal end side to a proximal end side along the tube 30 in the longitudinal direction (that is, an insertion axis O2 direction).

In addition to the flexible tube portion 25, the bending portion 24 may also be formed integrally using the tube 30 in place of the above-mentioned bending tube or the like.

A pair of bending operation knobs 26 for performing a bending operation of the bending portion 24 and a treatment instrument insertion portion 27 are formed on the operation section 22.

Further, from the operation section 22, a group of cables and tubes 28 such as an image guide bundle, a light guide bundle, a suction tube 28*a*, and a water feeding tube 28*b* extends.

In the baby endoscope 20 of the embodiment, an image pickup unit (not shown) may be disposed in the distal end portion 23 or in the operation section 22. In this case, a signal cable connected to the image pickup unit extends from the operation section 22 in place of the image guide bundle.

The operation section 22 includes a fixing band 29 for fixing the operation section 22 to the operation section 12 of the mother endoscope 10.

In the baby endoscope 20 having such a configuration, the tube 30 which forms the flexible tube portion 25 is formed of a multi-lumen tube including, for example, an observation hole 31 through which the image guide bundle (or the signal line of the image pickup unit), a light guide bundle and the like pass; a channel hole 32 which functions as a treatment instrument channel which is also used as a suction channel; a pair of water feeding holes 33 which is longitudinal direction holes; and four wire insertion holes 34 through which four wires (not shown) connected to the bending operation knobs 26 respectively pass. In the embodiment, the configuration is exemplified where the tube 30 includes the pair of water feeding holes 33. However, the number of water feeding holes 33 which are the longitudinal direction holes formed in the tube 30 may be one or three or more.

On a proximal end side of the tube 30, the treatment instrument insertion portion 27 and the suction tube 28a communicate with the channel hole 32, and the water feeding tube 28b communicates with the pair of water feeding holes 33. To realize the communication between these tubes, in the embodiment, a tube connector 41 which forms a frame member is connected to a proximal end side of the tube 30.

The tube connector 41 forms a tube module 40 together with the tube 30 (see FIG. 6, FIG. 8 and the like). Since the tube connector 41 is held in the operation section 22 (see FIG. 2), it is possible to connect a proximal end side of the tube 30 (that is, a proximal end side of the insertion section 21) to the operation section 22.

To allow the channel hole 32 and the pair of water feeding holes 33 to communicate with the tube connector 41, a channel communication hole 32a and a pair of water feeding communication holes 33a which forms first communication holes are formed on a proximal end side of the tube 30.

To describe more specifically, the channel communication hole 32a is a communication hole (side hole) which allows an inner surface of the channel hole 32 and an outer peripheral surface of the tube 30 to communicate with each other in a direction substantially perpendicular to the insertion axis O2, and the respective water feeding communication holes 33a are communication holes (side holes) which allow inner surfaces of the respective water feeding holes 33 and the outer peripheral surface of the tube 30 to communicate with each other in the direction substantially perpendicular to the insertion axis O2.

The channel communication hole 32a and the water feeding communication holes 33a are formed such that the positions of the communication holes are displaced from each other in the direction of the insertion axis O2 in a region on a proximal end side of the tube 30. In other words, in the embodiment, the channel communication hole 32a is formed at the position displaced toward a distal end side of the pair of water feeding communication holes 33a in the direction of the insertion axis O2. In the embodiment, the configuration is exemplified where the pair of water feeding communication holes 33a are formed in the tube 30 corresponding to the pair of water feeding holes 33. However, when the number of water feeding holes 33 which form the holes is one, the water feeding communication hole 33a which forms the first communication hole may be formed at one portion of the tube 30. Further, when the number of water feeding holes 33 which form the holes is three or more, the water feeding communication holes 33a which form the first communication holes may be formed at three or more portions of the tube 30 corresponding to the respective water feeding holes 33. Further, the water feeding communication hole 33a which is the first communication hole formed in the tube 30 may be respectively formed at two or more portions in the direction of the insertion axis O2 with respect to one water feeding communication hole 33a.

As shown in FIG. 4, the tube connector 41 has a cylindrical connector body 45.

A tube insertion hole 46 through which the tube 30 passes is formed in the connector body 45.

The tube insertion hole 46 is formed of a stepped through hole having an inner peripheral surface of an inner diameter larger than a diameter of the outer peripheral surface of the tube 30.

To describe more specifically, the tube insertion hole 46 is formed such that, for example, in order from a distal end side, a first insertion hole portion 46a having an inner diameter which is sufficiently larger than the outer diameter of the tube 30, a second insertion hole portion 46b having an inner diameter smaller than a diameter of the first insertion hole portion 46a (slightly larger than the outer diameter of the tube 30), a third insertion hole portion 46c having an inner diameter larger than a diameter of the second insertion hole portion 46b (for example, the same diameter as the first insertion hole portion 46a), and a fourth insertion hole portion 46d having an inner diameter larger than the third insertion hole portion 46c are connected with one another coaxially with the insertion axis O2.

Further, a channel branch tube 47 which communicates with the second insertion hole portion 46b and a water feeding branch tube 48 which communicates with the third insertion hole portion 46c are integrally formed with the connector body 45.

A channel branch conduit 47a is formed in the channel branch tube 47, and a distal end of the channel branch conduit 47a opens to an inner surface of the second insertion hole portion 46b. With such a configuration, the inner surface of the second insertion hole portion 46b communicates with the outside through the channel branch tube 47.

The channel branch tube 47 is disposed such that a proximal end side (branch end side) of the channel branch tube 47 protrudes from the operation section 22. Accordingly, the channel branch tube 47 functions as the treatment instrument insertion portion 27.

A suction branch tube 49 is branched from an intermediate portion of the channel branch conduit 47a. A suction branch conduit 49a which communicates with the channel branch conduit 47a is formed in the suction branch tube 49. In the operation section 22, a distal end side of the suction tube 28a can be connected to the suction branch tube 49.

In the water feeding branch tube 48, a water feeding branch conduit 48a which forms the second communication hole is formed. A distal end of the water feeding branch conduit 48a opens in the inner surface of the third insertion hole portion 46c. Accordingly, the inner surface of the third insertion hole portion 46c communicates with the outside through the water feeding branch tube 48. In the operation section 22, a distal end side of the water feeding tube 28b can be connected to the water feeding branch tube 48.

The first insertion hole portion 46a, on a distal end side of the connector body 45, has a function of holding O rings 55 which provides sealing between the outer peripheral surface of the tube 30 and the inner peripheral surface of the tube insertion hole 46.

In the first insertion hole portion 46a, for example, two O rings 55 are inserted from a distal end side of the connector body 45.

The second insertion hole portion 46b is formed with the diameter smaller than the diameter of the first insertion hole portion 46a and hence, on a proximal end of the first insertion hole portion 46a, a first stopper portion 46e which protrudes toward the inside of the tube insertion hole 46 is formed. Out of the pair of O rings 55, the O ring 55 positioned on the proximal end side is brought into contact with the first stopper portion 46e so that the movement of the O ring 55 toward the proximal end side is restricted and hence, positioning of the respective O rings 55 in the first insertion hole portion 46a is performed.

The respective O rings 55 inserted in this manner are brought into close contact with the outer peripheral surface of the tube 30 and the inner peripheral surface of the first insertion hole portion 46a and hence, a gap formed between the tube 30 and the first insertion hole portion 46a is sealed by the respective O rings 55 in an air-tight manner and in a liquid-tight manner.

The second insertion hole portion 46b is formed corresponding to the channel communication hole 32a which opens in the outer peripheral surface of the tube 30.

The tube 30 is positioned in the tube insertion hole 46 such that the channel communication hole 32a is positioned in the second insertion hole portion 46b. Accordingly, it is possible to allow the channel hole 32 formed in the tube 30 to communicate with the channel branch conduit 47a and the suction branch conduit 49a.

The third insertion hole portion 46c is formed corresponding to the water feeding communication holes 33a which open on the outer peripheral surface of the tube 30.

In the third insertion hole portion 46c, for example, an O ring 60 which forms the first sealing member, a spacer 61 having a cylindrical shape, an O ring 62 which forms the second sealing member, and an adjustment ring 63 having an annular shape are inserted in order from a proximal end side of the connector body 45.

The second insertion hole portion 46b is formed with the diameter smaller than the diameter of the third insertion hole portion 46c and hence, a second stopper portion 46f which is a stopper portion protruding toward the inside of the tube insertion hole 46 is formed on a distal end of the third insertion hole portion 46c. The O ring 60 is brought into contact with the second stopper portion 46f so that the movement of the O ring 60 toward a distal end side is restricted and hence, positioning of the O ring 60, the spacer 61, the O ring 62, and the adjustment ring 63 in the third insertion hole portion 46c is performed.

More specifically, the O ring 60 is brought into contact with the second stopper portion 46f and hence, the O ring 60 is positioned on a distal end side of the water feeding communication holes 33a and the water feeding branch conduit 48a in the third insertion hole portion 46c. The O ring 60 which is positioned in this manner is brought into close contact with the outer peripheral surface of the tube 30 and the inner peripheral surface of the third insertion hole portion 46c and hence, on a more distal end side than the water feeding communication holes 33a and the water feeding branch conduit 48a, a gap formed between the outer peripheral surface of the tube 30 and the third insertion hole portion 46c is sealed by the O ring 60 in an air-tight manner and in a liquid-tight manner.

The spacer 61 is brought into contact with the O ring 60 (that is, the spacer 61 is brought into contact with the second stopper portion 46f by way of the O ring 60) and hence, in the third insertion hole portion 46c, the spacer 61 is positioned at the position corresponding to the water feeding communication holes 33a and a distal end opening portion of the water feeding branch conduit 48a.

As shown in FIG. 8, FIG. 9, and FIG. 11, the spacer 61 has a wall portion 61a having an approximately cylindrical shape which is disposed between the tube 30 and the third insertion hole portion 46c (tube insertion hole 46) with predetermined gaps formed between the wall portion 61a and each of the tube 30 and the third insertion hole portion 46c (tube insertion hole 46). Further, communication holes 61b which form third communication holes for making an inner surface side and an outer surface side of the wall portion 61a communicate with each other are formed in the wall portion 61a of the spacer 61.

The spacer 61 including such communication holes 61b is disposed at the position which corresponds to the water feeding communication holes 33a and the distal end opening portion of the water feeding branch conduit 48a and hence, the pair of water feeding holes 33 formed in the tube 30 respectively communicate with the single water feeding branch conduit 48a.

The O ring 62 is brought into contact with the spacer 61 (that is, the O ring 62 is brought into contact with the second stopper portion 46f by way of the O ring 60 and the spacer 61) and hence, the O ring 62 is positioned on a proximal end side of the water feeding communication holes 33a and the water feeding branch conduit 48a in the third insertion hole portion 46c. The O ring 62 which is positioned in this manner is brought into close contact with the outer peripheral surface of the tube 30 and the inner peripheral surface of the third insertion hole portion 46c and hence, a gap formed between the outer peripheral surface of the tube 30 and the third insertion hole portion 46c is sealed in an air-tight manner and in a liquid-tight manner by the O ring 62 on a proximal end side of the water feeding communication holes 33a and the water feeding branch conduit 48a.

As shown in FIG. 4, in the embodiment, the O ring 60, the spacer 61, and the O ring 62 are integrally formed preliminarily.

The adjustment ring 63 is positioned at a proximal end in the third insertion hole portion 46c by being brought into contact with the O ring 62 (that is, being brought into contact with the second stopper portion 46f by way of the O ring 60, the spacer 61, and the O ring 62).

An end part member 70 which closes a proximal end side of the tube insertion hole 46 is held on the fourth insertion hole portion 46d.

To describe more specifically, for example, as shown in FIG. 10, a main part of the end part member 70 is an integral body formed of a lid body 71 which closes the fourth insertion hole portion 46d, and a cylindrical portion 72 which extends toward a proximal end side of the lid body 71.

A pin-shaped sealing member 73 is formed on a distal end surface of the lid body 71 in a protruding manner at the position which corresponds to the channel hole 32. By inserting the sealing member 73 into the channel hole 32, a proximal end side of the channel hole 32 is sealed, and a proximal end side of the tube 30 is connected to the end part member 70.

In connecting the tube 30 to the end part member 70, the pin-shaped sealing members 74 are respectively inserted into proximal end portions of the respective water feeding holes 33. Accordingly, proximal end sides of the respective water feeding holes 33 are sealed.

Further, the through holes 71a and 71b which penetrate the lid body 71 in the direction of the insertion axis O2 are formed in the lid body 71. The through holes 71a and 71b are disposed at positions corresponding to the observation hole 31 and the respective wire insertion holes 34. By connecting the end part member 70 to a proximal end side of the tube 30 by way of the sealing members 74, the observation hole 31 and respective wire insertion holes 34 communicate with an inner portion (inside) of the cylindrical portion 72 through the respective through holes 71a, 71b. By making the observation hole 31 and the respective wire insertion holes 34 communicate with the inner portion of the cylindrical portion 72 through the respective through holes 71a, 71b in this manner, it is possible to insert the image guide bundle and the light guide bundle into the observation hole 31 and to insert wires to the respective wire insertion holes 34 from the inside of the cylindrical portion 72.

A pair of cutout portions 72a is formed on an outer peripheral surface of the cylindrical portion 72. A flange portion 72b which protrudes outward in a radial direction is formed on a proximal end portion of the cylindrical portion 72 in a region except the cutout portions 72a.

A pair of locking pawl portions 50 is formed on a proximal end portion of the connector body 45 corresponding to these cutout portions 72a and the flange portion 72b.

These locking pawl portions 50 are locked to a proximal end of the cylindrical portion 72 and hence, the lid body 71 of the end part member 70 is held in the fourth insertion hole portion 46d.

In this case, the tube 30 is pushed into the tube insertion hole 46 by the end part member 70 and hence, the positioning of the proximal end position of the tube 30 with respect to the connector body 45 in the direction of the insertion axis O2 is automatically performed. Accordingly, the positioning of the tube 30 in the direction of the insertion axis O2 in the tube insertion hole 46 is automatically performed and hence, the channel communication hole 32a is disposed in the second insertion hole portion 46b, and the water feeding communication holes 33a are disposed in the third insertion hole portion 46c (see FIG. 8 and FIG. 9).

By sandwiching the cutout portions 72a and the flange portion 72b between the pair of locking pawl portions 50, positioning of the rotational position of the end part member 70 about the insertion axis O2 is performed. Along with the positioning of the rotational position of the end part member 70, the positioning of the rotational position of the tube 30 about the insertion axis O2 in the tube insertion hole 46 is automatically performed. Accordingly, in the second insertion hole portion 46b, the channel communication hole 32a is disposed at the position where the channel communication hole 32a agrees with the distal end opening of the channel branch conduit 47a (see FIG. 8).

Further, the O ring 60, the spacer 61, and the O ring 62 are sandwiched between the second stopper portion 46f and the end part member 70 by way of the adjustment ring 63. Accordingly, the O ring 60, the spacer 61, and the O ring 62 are held in a state where these members are positioned at predetermined positions with reference to the second stopper portion 46f (see FIG. 7 to FIG. 9 and FIG. 11).

In assembling such a tube module 40, for example, as shown in FIG. 5, the pair of O rings 55 is inserted into the tube insertion hole 46 (first insertion hole portion 46a) from a distal end side of the connector body 45.

Further, with respect to the tube 30, the O ring 60, the spacer 61, the O ring 62, and the adjustment ring 63 are temporarily assembled to the tube 30.

Further, the sealing members 74 are inserted into the respective water feeding holes 33 of the tube 30 and hence, the proximal end sides of the respective water feeding holes 33 are sealed.

The channel hole 32 is inserted by the sealing member 73 and hence, the proximal end side of the channel hole 32 is sealed, and the end part member 70 is connected to the proximal end of the tube 30.

Then, in a state where the O ring 60, the spacer 61, the O ring 62, and the adjustment ring 63 are temporarily assembled in this manner, and the end part member 70 is connected to the tube 30, the tube 30 is inserted into the tube insertion hole 46 from a proximal end side of the connector body 45.

Then, when the end part member 70 engages with the pair of locking pawl portions 50, the tube 30, the O ring 60, the spacer 61, the O ring 62, and the adjustment ring 63 are automatically positioned in the tube insertion hole 46. Accordingly, the channel hole 32 formed in the tube 30 communicates with the channel branch conduit 47a and the suction branch conduit 49a, and the water feeding holes 33 formed in the tube 30 communicate with the water feeding branch conduit 48a.

According to such an embodiment, the endoscope 1 includes: the tube 30 which has the water feeding holes 33 extending from the distal end side to the proximal end side along the tube 30 in the longitudinal direction and including the water feeding communication holes 33a which allow the inner surfaces of the water feeding holes 33 to communicate with the outside and opens on the outer peripheral surface of the tube 30; the tube connector 41 which includes the tube insertion hole 46 having the inner peripheral surface of the inner diameter larger than the outer diameter of the outer peripheral surface of the tube 30, in which the water feeding branch conduit 48a which allows the inner surface of the tube insertion hole 46 (the third insertion hole portion 46c) to communicate with the outside is formed, and in which the second stopper portion 46f which protrudes toward the inside of the tube insertion hole 46 is formed on a distal end side of the water feeding branch conduit 48a; the O ring 60 which is disposed between the tube 30 and the tube insertion hole 46 in a state where the O ring is positioned on a distal end side of the water feeding communication holes 33a and the distal end opening of the water feeding branch conduit 48a by contacting with the second stopper portion 46f, and is brought into close contact with the outer peripheral surface of the tube 30 and the inner peripheral surface of the tube insertion hole 46; the spacer 61 which is disposed between the tube 30 and the tube insertion hole 46 with a predetermined gap therebetween in a state where the wall portion 61a is positioned at the position corresponding to the water feeding communication holes 33a and the distal end opening of the water feeding branch conduit 48a by contacting with the O ring 60, and in which the communication holes 61b which allow the inner surface side and the outer surface side of the wall portion 61a to communicate with each other are formed; and the O ring 62 which is disposed between the tube 30 and the tube insertion hole 46 in a state where the O ring 62 is positioned on a proximal end side of the water feeding communication holes 33a and the distal end opening of the water feeding branch conduit 48a by contacting with the spacer 61, and is brought into close contact with the outer peripheral surface of the tube 30 and the inner peripheral surface of the tube insertion hole 46.

With such a simple configuration and steps, it is possible to allow the water feeding communication holes 33a formed in the tube 30 to communicate with the water feeding branch conduit 48a by means of the O rings 60 and 62.

In other words, using the second stopper portion 46f formed in the tube insertion hole 46 and the spacer 61 inserted into the tube insertion hole 46, the O rings 60, 62 are positioned with respect to the water feeding communication holes 33a of the water feeding holes 33 and the distal end opening of the water feeding branch conduit 48a, and the water feeding communication holes 33a side and the water feeding branch conduit 48a side are made to communicate with each other through the communication holes 61b formed in the wall portion 61a of the spacer 61. Accordingly, with the simple configuration and steps, while providing sealing of the water feeding communication holes 33a and the distal end side and the proximal end side of the water feeding branch conduit 48a, a cleaning liquid or the like which is supplied through the water feeding branch tube 48 can be supplied to the water feeding holes 33, and the cleaning liquid or the like is ejected from the water feeding nozzles 23c (see FIG. 11 and FIG. 12).

The present invention is not limited to the embodiment described above, and various modifications and alternations are conceivable, and these modifications and alternations also fall within the technical scope of the present invention.

Figure 13:
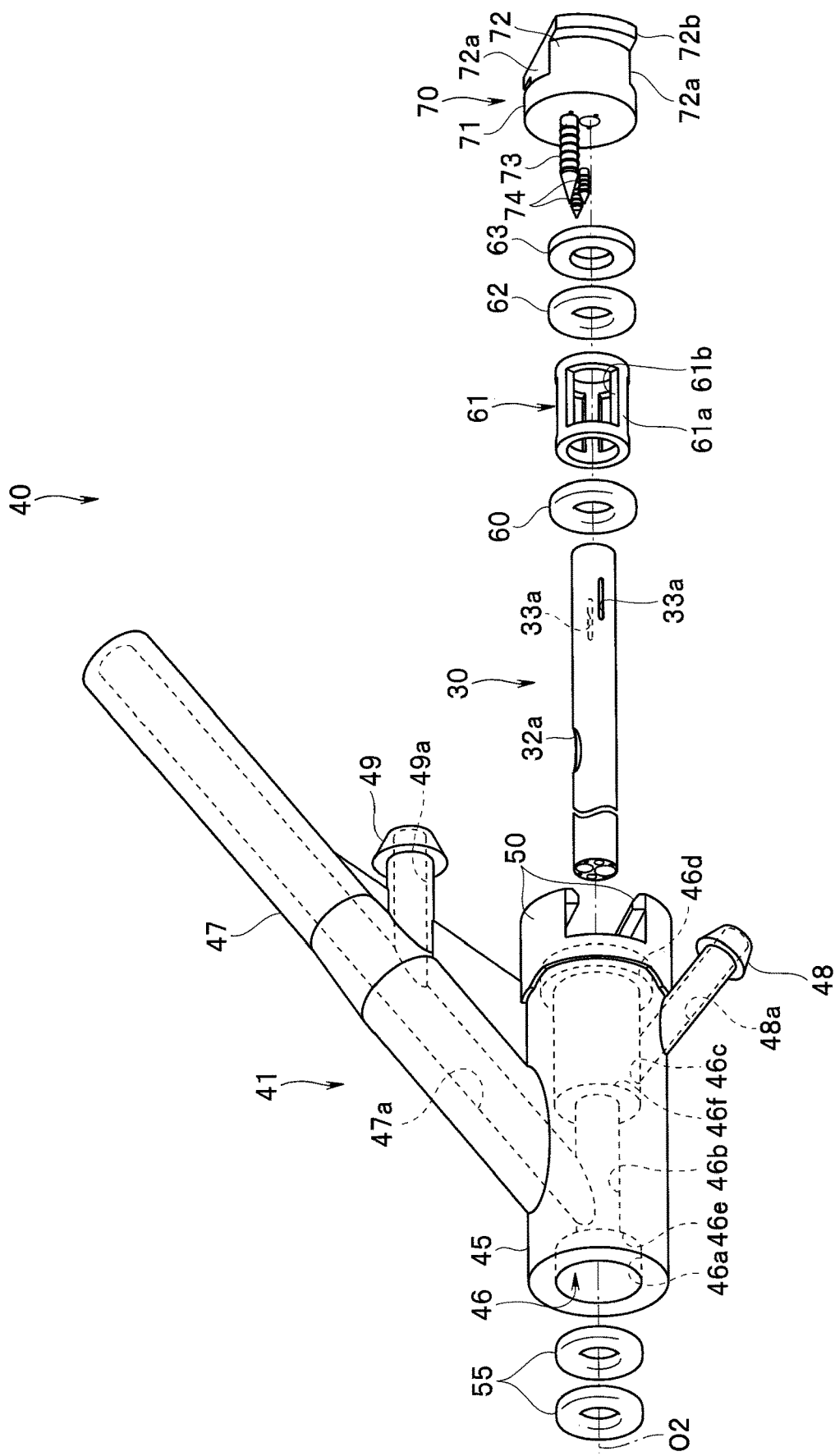
FIG. 13 is an exploded perspective view of a tube module according to a modification.

For example, in the above-mentioned embodiment, the case is exemplified where the O ring 60, the spacer 61, and the O ring 62 are preliminarily formed integrally. However, the present invention is not limited to such a configuration. For example, as shown in FIG. 13, the O ring 60, the spacer 61, and the O ring 62 may be formed as separate bodies from one another. Alternatively, only the O ring 60 and the spacer 61 may be integrally formed with each other or only the spacer 61 and the O ring 62 may be integrally formed with each other preliminarily.

In the above-mentioned embodiment, the example is given where the configuration of the present invention is applied to the endoscope (baby endoscope). However, the present invention is not limited to such an example. For example, it goes without saying that the present invention is also applicable to an insertion apparatus such as a catheter or a sheath which uses a tube such as a multi-lumen tube.

Needless to say, the configuration of the present invention is not limited to the communication of the water feeding hole.

What is claimed is:

1. An endoscope comprising:
   an insertion section having a tube comprising:
      a first tube conduit extending longitudinally from a distal end side to a proximal end side of the tube;
      a second tube conduit extending longitudinally from the distal end side to the proximal end side of the tube;
      a first tube communication hole formed on an outer circumferential surface of the tube, the first tube communication hole allowing the first tube conduit to fluidly communicate with an outside of the tube; and
      a second tube communication hole formed on the outer circumferential surface of the tube offset longitudinally from the first communication hole, the second communication hole communicating with the second tube conduit,
   a frame comprising:
      a first frame conduit into which the tube is inserted; and
      a second frame conduit which allows the first tube conduit to fluidly communicate with an outside of the frame; and
      a third frame conduit which allows the second tube conduit to fluidly communicate with the outside of the frame; and
   a spacer mounted on the outer circumferential surface of a proximal end side of the tube, the spacer being positioned in the first frame conduit such that the first tube communication hole and the second frame conduit fluidly communicate with each other and the second tube communication hole and the third frame conduit fluidly communicate with each other.

2. The endoscope according to claim 1, wherein
   a first seal and a second seal are disposed to sealingly contact with the tube and with the first frame conduit,
   the spacer is disposed between the first seal and the second seal, and
   the second frame conduit has an opening at a longitudinal position of the first frame conduit between the first seal and the second seal.

3. The endoscope according to claim 2, wherein one or more of the first seal and the second seal is integrally formed with the spacer.

4. The endoscope according to claim 2, wherein the first seal, the second seal, and the spacer are integrally formed with one another.

5. The endoscope according to claim 2, wherein one of a first position of the first seal and a second position of the second seal is movable in a longitudinal direction in the first frame conduit.

6. The endoscope according to claim 2, further comprising a third seal disposed on a proximal end side of the first tube conduit for sealing the proximal end side of the first tube conduit.

7. The endoscope according to claim 1, further comprising a lid body provided proximally relative to the proximal end side of the tube, the lid body engaging the frame so as to close a proximal opening of the first tube conduit.

8. The endoscope according to claim 7, wherein the lid body having a seal for sealing the proximal opening of the first tube conduit.

9. The endoscope according to claim 7, wherein the lid body being configured to pass one or more of an image guide bundle, a light guide bundle and a wire through one or more respective openings formed in the lid body.

10. The endoscope according to claim 7, the lid body is configured to restrict a motion of the tube along a longitudinal direction and to restrict a rotation of the tube around a radial direction.

11. The endoscope according to claim 1, wherein the tube is a multi-lumen tube having a plurality of lumens, the plurality of lumens including the first tube conduit and the second tube conduit.

12. The endoscope according to claim 1, wherein
   the first tube communication hole and the second frame conduit are configured to feed a fluid from the proximal end side to the distal end side, and
   the second tube communication hole and the third frame conduit are configured to insert a treatment tool.

13. The endoscope according to claim 1, wherein the first tube communication hole comprises a plurality of first tube communication holes and the first tube conduit comprises a plurality of first tube conduits, each of the plurality of first tube communication holes formed on the outer circumferential surface of the tube, the plurality of first tube communication holes allowing a respective one of the plurality of first tube conduits to fluidly communicate with an outside of the tube.

14. The endoscope according to claim 1, wherein a first opening of the second tube communication hole and a second opening of the third frame conduit are configured to face each other.

15. The endoscope according to claim 1, wherein the tube is inserted into one of a side view type endoscope and an oblique view type endoscope.

16. The endoscope according to claim 1, wherein the first tube communication hole and the second tube communication hole allowing each of the first and second tube conduits to separately fluidly communicate with the outside of the tube.

17. An endoscope comprising:
a frame having a common conduit;
a tube inserted in the common conduit; and
a seal for sealing a first passage from a second passage;
the first passage comprising:
   a first tube conduit formed in the tube to extend longitudinally from a distal end side to a proximal end side of the tube;
   a first communication hole formed on an outer circumferential surface of the tube at a first position inside the common conduit, the first communication hole being in fluid communication with the first tube conduit; and
   a first frame conduit formed in the frame, the first frame conduit being in fluid communication with the first communication hole and the first tube conduit;
the second passage comprising:
   a second tube conduit, different from the first tube conduit, formed in the tube, the second tube conduit extending longitudinally from the distal end side to the proximal end side of the tube;
   a second communication hole formed on an outer circumferential surface of the tube at a second position inside the common conduit, the first and second positions being longitudinally offset from each other, the second communication hole being in fluid communication with the second tube conduit; and
   a second frame conduit formed in the frame, the second frame conduit being in fluid communication with the second communication hole and the second tube conduit.

18. The endoscope according to claim 17, further comprising a lid body provided proximally relative to the proximal end side of the tube, the lid body engaging the frame so as to close a proximal opening of the first tube conduit.

19. The endoscope according to claim 18, wherein the lid body being configured to pass one or more of an image guide bundle, a light guide bundle and a wire through one or more respective openings formed in the lid body.

20. The endoscope according to claim 17, wherein
the first communication hole and the second frame conduit are configured to feed a fluid from the proximal end side to the distal end side, and
the second communication hole and the second frame conduit are configured to insert a treatment tool.

21. An endoscope comprising:
an insertion section having a tube comprising:
   a first tube conduit extending longitudinally from a distal end side to a proximal end side of the tube;
   a second tube conduit extending longitudinally from the distal end side to the proximal end side of the tube;
   a first tube communication hole formed on an outer surface of the tube, the first tube communication hole allowing the first tube conduit to fluidly communicate with an outside of the tube; and
   a second tube communication hole formed on the outer surface of the tube offset longitudinally from the first communication hole, the second communication hole communicating with the second tube conduit,
a frame comprising:
   a first frame conduit into which the tube is inserted; and
   a second frame conduit which allows the first tube conduit to fluidly communicate with an outside of the frame; and
   a third frame conduit which allows the second tube conduit to fluidly communicate with the outside of the frame; and
a spacer mounted on the outer surface of a proximal end side of the tube, the spacer being positioned in the first frame conduit such that the first tube communication hole and the second frame conduit fluidly communicate with each other and the second tube communication hole and the third frame conduit fluidly communicate with each other;
wherein
a first seal and a second seal are disposed to sealingly contact with the tube and with the first frame conduit,
the spacer is disposed between the first seal and the second seal, and
the second frame conduit has an opening at a longitudinal position of the first frame conduit between the first seal and the second seal.

* * * * *